US00PP23902P3

(12) United States Plant Patent
Zaiger et al.

(10) Patent No.: US PP23,902 P3
(45) Date of Patent: Sep. 17, 2013

(54) INTERSPECIFIC TREE NAMED 'FLAVOR FUSION'

(50) Latin Name: ***Prunus* species**
Varietal Denomination: Flavor Fusion

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 378 days.

(21) Appl. No.: 13/066,528

(22) Filed: Apr. 18, 2011

(65) Prior Publication Data

US 2012/0266337 P1 Oct. 18, 2012

(51) Int. Cl.
*A01H 5/00* (2006.01)

(52) U.S. Cl.
USPC ..... Plt./180; Plt./184

(58) Field of Classification Search
USPC ..... Plt./180, 184
See application file for complete search history.

*Primary Examiner* — June Hwu
*Assistant Examiner* — Louanne Krawczewicz Myers

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Heavy and regular bearer of fruit.
3. Fruit with very good flavor and eating quality.
4. Fruit with attractive red skin color.
5. Fruit with good handling and shipping quality.

1 Drawing Sheet

Botanical classification: Interspecific *Prunus* species.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of proprietary interspecifics and apricot trees, which are known to us, and mentioned herein, 19M42, 326LC131, 43GK21, 31Z635, 38GH76, 20Z62, 4G1180 and the Interspecific 'Bella Sun' (U.S. Plant Pat. No. 21,817).

STATEMENT REGARDING FEDERALLY SPONSORED RESEARCH AND DEVELOPMENT

Not applicable.

ORIGIN OF THE VARIETY

The new and distinct variety of interspecific tree was originated by us from crosses between the following species [*Prunus salicina*×(*Prunus salicina*×*Prunus armeniaca*) and *Prunus armeniaca*]. The present variety is a first generation cross between the proprietary interspecific seedling with the field identification number '19M42' and 'Bella Sun' Interspecific (U.S. Plant Pat. No. 21,817). The seed parent (19M42) was developed by us from crosses of the following proprietary interspecific seedling selections 326LC131, 43GK21, 20Z62, 31Z635, 38GH71 and 4G1180. We budded a large number of these seedlings to older trees of 'Nemaguard' Rootstock (non-patented) to induce earlier fruit production for evaluation. Under close and careful observation, one seedling, which is the present variety exhibited desirable fruit and tree characteristics and was selected in 2007 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree, which includes plums, plumcots and apricots in its parentage, is of large size, vigorous upright growth and a productive and regular bearer of medium to large size fruit with very good flavor and eating quality. The fruit is further characterized by having attractive red skin, firm, red flesh and having good storage and shipping quality. In comparison to its seed parent (19M42) the fruit of the new variety has darker red skin color and is 12 days earlier in maturity. In comparison to its pollen parent 'Bella Sun' Interspecific (U.S. Plant Pat. No. 21,817) the fruit of the new variety has red skin and flesh color, compared to yellow and has glabrous skin compared to pubescent. In comparison to the commercial Interspecific 'Amigo I' (U.S. Plant Pat. No. 20,165) the fruit of the new variety has red flesh compared to yellow and red flesh, is larger in size and is 8 days earlier in maturity.

PHOTOGRAPH OF THE VARIETY

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large, pruned to 3 to 3.5 meters in height and width for economical harvesting of fruit.

*Vigor.*—Vigorous, tree growth of approximately 1.5 to 2 meters the first growing season, varies with soil type, fertility and cultural practices.

*Form.*—Upright, usually pruned to vase shape.

*Branching habit.*—Upright, crotch angle approximately 40°, increases with heavy crop load.

*Productivity.*—Productive, thinning and spacing necessary for desirable market size. Fruit set varies with climatic conditions at bloom time.

*Bearer.*—Regular, adequate fruit set 4 consecutive years. No alternate bearing observed.

*Fertility.*—Self-sterile, pollinator required.

*Density.*—Medium dense, usually pruned to vase shape to increase sunlight to center of tree to enhance fruit color and health of fruit spurs.

*Hardiness.*—Hardy in all stone fruit growing areas of California. Tree grown in USDA Hardiness Zone 9. Winter chilling requirement approximately 650 hours at or below 45° F.

Trunk:

*Size.*—Medium to large. Average circumference 52.1 cm at 25.4 cm above ground on a 6 year old tree.

*Stocky.*—Medium stocky.

*Texture.*—Medium shaggy, roughness increases with age.

*Color.*—Varies from 7.5YR 6/2 to 10YR 4/2.

Branches:

*Size.*—Medium. Average circumference 11.4 cm at 1.2 meters above the ground. Crotch angle approximately 40°, increases with heavy crop load.

*Surface texture.*—New growth relatively smooth. Mature growth medium rough, roughness increases with age.

*Lenticels.*—Size — medium. Average number 97 in a 25.8 sq cm section. Average length 2.2 mm. Average width 1.4 mm. Color varies from 7.5YR 4/8 to 10YR 5/8.

*Color.*—New growth varies from 5GY 5/8 with 5R 2/6 where exposed to the sun. Old growth varies from 5YR 2/4 to 5YR 5/2, varies with age of growth.

Leaves:

*Size.*—Medium. Average length 107.4 mm. Average width 58.2 mm.

*Form.*—Oblanceolate.

*Apex.*—Acuminate.

*Base.*—Cuneate.

*Margin.*—Doubly serrate.

*Thickness.*—Medium.

*Surface texture.*—Upper surface relatively smooth, slight indentations over midrib and leaf veins, glabrous. Lower surface relatively smooth, except for small ridges created by midrib and pinnate venation, glabrous.

*Petiole.*—Medium length. Average length 13.6 mm. Average width 1.9 mm. Longitudinally grooved. Surface — glabrous. Color varies from 5GY 5/8 with 7.5R 3/4 where exposed to sun.

*Glands.*—Type — globose. Size — small. Average length 0.9 mm. Average diameter 0.6 mm. Average number 4, varies from 1 to 8. Located on base of the leaf blade and upper portion of the petiole. Color varies from 10Y 6/6 to 2.5GY 6/6.

*Stipules.*—Average number 1. Average length. 10.6 mm. Edges — serrulate. Color varies from 2.5GY 7/6 to 5GY 7/6.

*Color.*—Upper surface varies from 5GY 4/8 to 5GY 3/6. Lower surface varies from 5GY 4/4 to 7.5GY 4/4. Midvein color varies from 2.5GY 6/6 to 5GY 7/6.

Flower buds:

*Size.*—Small to medium. Average length 8.0 mm. Average diameter 5.0 mm.

*Hardiness.*—Hardy with respect to California winters.

*Form.*—Conical, becoming elongated before opening.

*Pedicel.*—Average length 10.7 mm. Averaged width 0.8 mm. Color varies from 2.5GY 7/6 to 2.5GY 7/8. Surface — glabrous.

*Color.*—N 9.5/ (white).

*Number of buds per spur.*—Average number 11, varies with age of spur.

Flowers:

*Blooming period.*—Date of First Bloom Feb. 22, 2010. Date of Petal Fall Mar. 4, 2010, varies slightly with climatic conditions.

*Size.*—Small. Average height 10.6 mm. Average diameter 16.6 mm.

*Petals.*—Size — small. Number — normally 5, alternately arranged to sepals. Average length 9.3 mm. Average width 6.7 mm. Form — orbicular to slightly elliptical. Margin — sinuate. Color — N 9.5/ (white). Both surfaces glabrous.

*Sepals.*—Size — small. Number — normally 5, alternately arranged to petals. Average length 2.6 mm. Average width 2.7 mm. Form — triangular. Margin — entire. Color — upper surface varies from 2.5GY 6/8 to 5GY 6/8. Lower surface varies from 5GY 6/6 to 5GY 5/6. Both upper and lower surface glabrous.

*Stamens.*—Average number per flower 25. Average filament length 7.3 mm. Filament color N 9.5/ (white). Anther color 5Y 8/10.

*Pollen.*—Self sterile, pollinator required. Color varies from 5Y 7/10 to 5Y 7/12.

*Pistil.*—Normally one. Surface — glabrous. Average length 8.9 mm. Stigma height approximately 0.9 mm below anthers. Color varies from 10Y 8/8 to 2.5GY 8/6.

*Fragrance.*—Heavy aroma.

*Color.*—N 9.5/ (white).

*Number flowers per flower bud.*—Average number 2, varies from 1 to 4.

*Pedicel.*—Average length 12.4 mm. Average width 0.8 mm. Color varies from 2.5GY 6/6 to 2.5GY 6/8. Surface — glabrous.

Fruit:

*Maturity when described.*—Firm ripe.

*Date of first picking.*—Jun. 7, 2010.

*Date of last picking.*—Jun. 15, 2010, varies slightly with climatic conditions.

*Size.*—Medium to large. Average diameter axially 54.3 mm. Average transversely in suture plane 60.1 mm. Average weight 127.8 grams, varies slightly with fertility of the soil, amount of thinning and climatic conditions.

*Form.*—Globose.

*Suture.*—Nearly smooth, extends from base to apex.

*Ventral surface.*—Very slightly lipped.

*Apex.*—Rounded.

*Base.*—Flat to slightly retuse.

*Stem cavity.*—Rounded to slightly elongated in suture plane. Average depth 5.1 mm. Average diameter 6.6 mm.

Stem:

*Size.*—Medium to large. Average length 16.8 mm. Average diameter 1.7 mm.

*Color.*—Varies from 5GY 5/6 to 5GY 5/8.

Flesh:

*Ripens.*—Evenly.

*Texture.*—Firm, meaty.

*Fibers.*—Few, small, tender.

*Firmness.*—Firm, comparable to other commercial interspecific varieties.

*Aroma.*—Moderate.

*Amydgalin.*—Undetected.

*Eating quality.*—Very good.

*Flavor.*—Very good, good balance between acid and sugar.

*Juice.*—Moderate amount, enhances flavor.

*Brix.*—Average 11.7°, varies slightly with amount of fruit per tree and climatic conditions.

*Color.*—Varies from 5R 4/2 to 7.5R 4/10. Stone cavity varies from 7.5R 3/8 to 7.5R 3/10.

Skin:

*Thickness.*—Medium.

*Surface.*—Smooth.

*Bloom.*—Moderate amount, complete coverage.

*Tendency to crack.*—None.

*Color.*—Ground color varies from 7.5Y 9/4 to 10Y 7/4. Overspread with 7.5R 3/10 to 7.5R 2/8.

*Tenacity.*—Tenacious to flesh.

*Astringency.*—Undetected.

Stone:

*Type.*—Clingstone.

*Size.*—Medium. Average length 25.1 mm. Average width 19.8 mm. Average thickness 9.9 mm.

*Form.*—Ovoid.

*Base.*—Relatively flat, varies from flat to rounded.

*Apex.*—Pointed. Average length 2.3 mm.

*Surface.*—Slightly pitted throughout. A small groove on each side of suture.

*Sides.*—Unequal, one side extended further from suture plane.

*Ridges.*—Small narrow ridges extending from base to apex.

*Tendency to split.*—None.

*Color.*—Varies from 7.5YR 6/6 to 7.5YR 5/8 when dry.

Kernel:

*Size.*—Small to medium. Average length 12.8 mm. Average width 9.2 mm. Average depth 4.9 mm.

*Form.*—Ovate.

*Viability.*—Partially viable, some embryos not fully developed.

*Skin.*—Color varies from 10YR 6/8 to 2.5Y 8.5/4.

Use: Dessert.

*Market.*—Local and long distance.

Keeping quality: Good, held firm in cold storage for 2 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

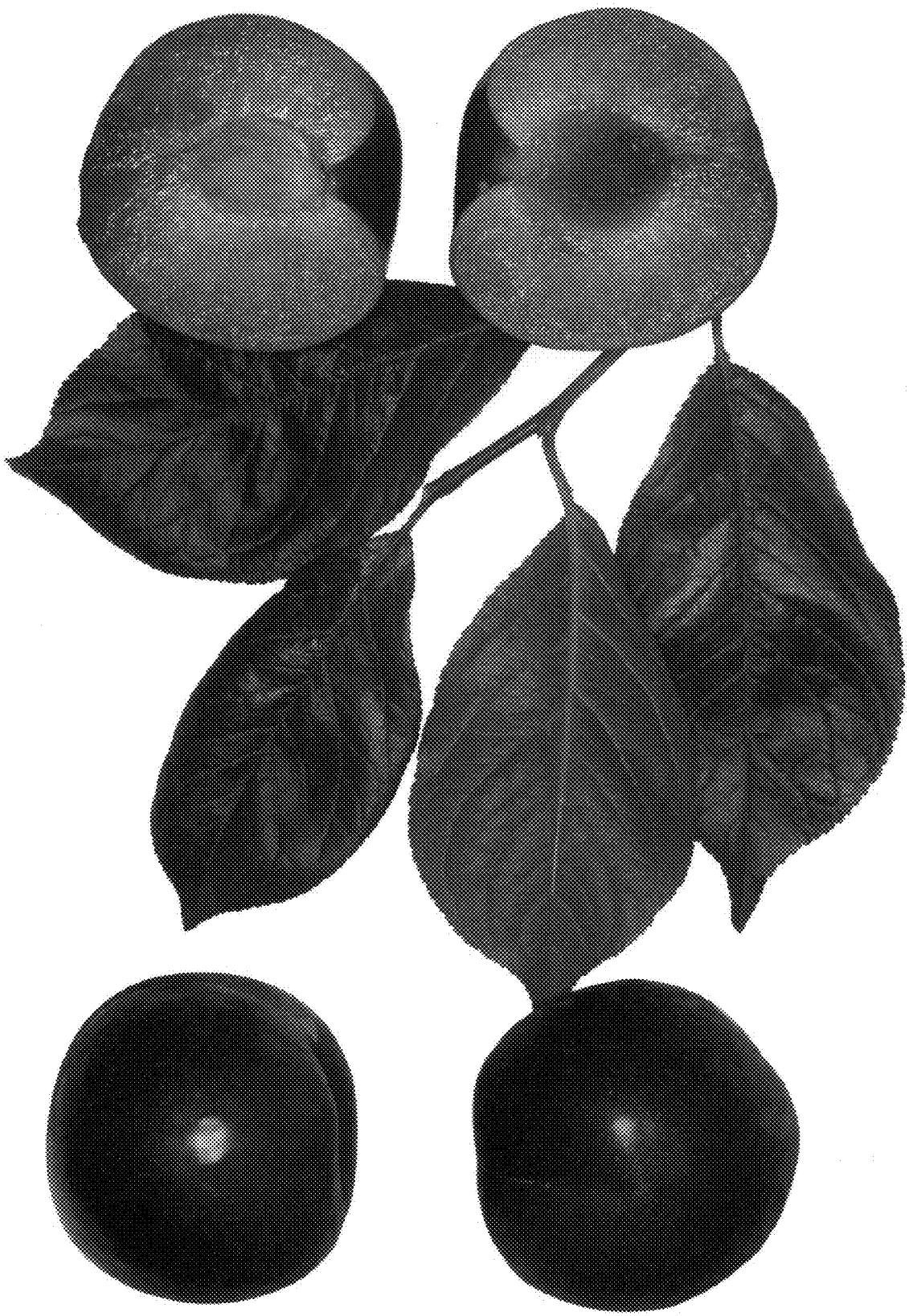

* * * * *